United States Patent [19]

Murray et al.

[11] Patent Number: 5,087,752
[45] Date of Patent: Feb. 11, 1992

[54] SYNTHESIS OF NITROXIDES USING DIOXIRANES

[75] Inventors: Robert W. Murray, Creve Coeur; Megh Singh, Normandy, both of Mo.

[73] Assignee: Curators of the University of Missouri, Columbia, Mo.

[21] Appl. No.: 581,520

[22] Filed: Sep. 12, 1990

Related U.S. Application Data

[63] Continuation-in-part of Ser. No. 407,116, Sep. 14, 1989, abandoned.

[51] Int. Cl.$^5$ ............................................. C07C 283/04
[52] U.S. Cl. ..................................... 564/298; 540/29; 546/184; 546/188; 548/216; 548/531; 548/537; 564/297; 564/299; 252/182.12
[58] Field of Search ............... 564/298; 546/184, 188; 548/216, 531, 537

[56] References Cited

PUBLICATIONS

Murray, Robert W. et al., "A New Synthesis of Nitro Compounds Using Dimethyldioxirane", *Tetrahedron Letters* 27 (21): 2335-2336 (1986).
Rauckman, Elmer J. et al., "Improved Method for the Oxidation of Secondary Amines to Nitroxides", *Synthetic Communications*, 409-413 (1975).
Murray, Robert W. and Singh, Megh, "A Convenient High Yield Synthesis of Nitroxides", *Tetrahedron Letters* 29 (37): 4677-4680 (Oct. 1988).
Murray, Robert W. et al., "Dioxiranes: Synthesis and Reactions of Methyldioxiranes", *The Journal of Organic Chemistry 50*: 2847-2853 (1985).
"Nitroxide Spin Labels Biochemical Reporter Groups", 1572-1574, (1988-1989 Catalog, Aldrich Chemical Co., Milwaukee, WI).

*Primary Examiner*—Robert T. Bond
*Attorney, Agent, or Firm*—Haverstock, Garrett and Roberts

[57] ABSTRACT

The subject invention relates to a method of synthesizing nitroxides from secondary amines. This method uses a suitable dioxirane compound such as dimethyldioxirane (DMD), which is relatively stable and simple to synthesize, as the oxidizing agent. A quantity of a secondary amine having no hydrogen atoms directly attached to the alpha carbon atoms is mixed with a 2x molar ratio of the dioxirane. In a first reaction, the secondary amine is oxidized to form a hydroxylamine; in a second reaction, the hydroxylamine is further oxidized to form a nitroxide. When the dioxirane loses an oxygen atom it converts into a ketone; for example, dimethyldioxirane is converted into acetone. This is very convenient, since the ketone byproduct is a solvent that can be easily removed after the reaction without causing interfering reactions. This method provides a simple, highly selective, rapid reaction with very high yields. It can be carried out in a single reaction vessel and can be used with a wide variety of secondary amines (including secondary amines having more than one amine group) to create a corresponding variety of nitroxides.

17 Claims, 1 Drawing Sheet

SYNTHESIS OF NITROXIDES USING DIOXIRANES

GOVERNMENT SUPPORT

This invention was made with government support under Grant 5 R01 ES 01984, awarded by the National Institute of Environmental Health Science.

This application is a continuation-in-part of U.S. application Ser. No. 407,116, filed Sept. 14, 1989 now abandoned.

FIELD OF THE INVENTION

This invention is in the field of organic chemistry, and relates to the synthesis of nitroxides of secondary amines.

BACKGROUND OF THE INVENTION

Dioxirane compounds have the following structure:

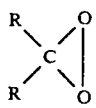

Although dioxirane itself, $H_2CO_2$, is not stable, various other dioxirane derivatives have been isolated in stable form. Dimethyldioxirane (DMD) was first isolated by Murray and his coworkers, and a method for synthesizing DMD in acetone solution is described in Murray et al 1985 (full citations are provided below). Various other dioxiranes have also been isolated, including methylethyldioxirane and diethyldioxirane (Murray et al 1985) and trifluoromethylmethyl dioxirane (Mello et al 1988). Dioxirane chemistry is relatively new, yet it is already possible to synthesize dioxirane compounds having a variety of structures, depending on the structures of their ketone precursors. More elaborate dioxiranes, such as dioxiranes having cyclic ring structures, can probably be synthesized and isolated as well, using methods that are currently known or hereafter discovered.

Dioxiranes are powerful oxidizing agents. For example, DMD has been used to oxidize primary amines, forming nitro compounds (Murray et al 1986). Eaton et al 1988 reported that dioxirane can be used to oxidize sensitive primary amines if the amine hydrochloride rather than the free amine is used. Zabrowski et al 1988 reports the use of dioxirane to oxidize substituted anilines to form nitro compounds. Prior to the subject invention, they had not been used to create nitroxides.

Nitroxides of Secondary Amines

Nitroxides derived from secondary amines are useful in a variety of reactions, since they can form relatively stable "free radical" groups, i.e., molecules having unpaired electrons which can exist for prolonged periods at temperatures above freezing. The free radical group makes them easily detectable in certain analytical processes, such as electron spin resonance (ESR, also referred to as electron paramagnetic resonance, EPR). This makes them useful as "spin labels" in probing biological structures (Berliner 1976 and Holtzman 1984), and as magnetic resonance imaging (MRI) contrast-enhancing agents (Keana et al 1985). They are also used to stabilize some polymers against degradation by light (Klemchuk 1985).

Previous Methods of Synthesizing Nitroxides

Prior methods of synthesizing nitroxides from secondary amines are discussed in Keana et al 1967, Rozantsev 1970, Rauckman et al 1975, and Keana et al 1984. Some of those methods involve meta-chloroperbenzoic acid as the oxidizing agent; others involve a combination of hydrogen peroxide and either tungstic, molybdic, or vanadic acid. Long reaction times (usually several hours) are required, and some of those methods operate in aqueous systems, which requires either a water soluble secondary amine or the use of phase transfer catalysts. Yields are usually not very high, and the reactions often generate unwanted by-products which may be very difficult yet necessary to remove before the desired nitroxides can be used for biological purposes. In addition, the prior methods require reagents that are expensive and/or difficult to synthesize.

The present invention, by contrast, provides a general method for synthesizing nitroxides from secondary amines. This method offers a simple process which can be conducted in a single reaction vessel, with very high yields and little or no unwanted by-products. It has been shown to work satisfactorily with various types of secondary amine reagents, including aliphatic, aromatic, cyclic, and heterocyclic secondary amines. The secondary amine group is oxidized very selectively; therefore, there is no need to take special steps to protect and then deprotect other reactive groups.

SUMMARY OF THE INVENTION

The subject invention relates to a method of synthesizing nitroxides from secondary amines. This method uses a suitable dioxirane compound such as dimethyldioxirane (DMD), which is relatively stable and simple to synthesize, as the oxidizing agent. The reaction proceeds as follows:

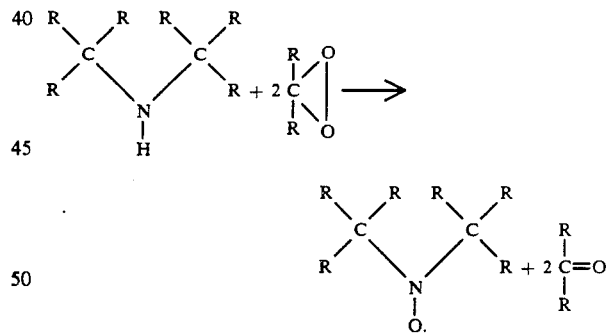

In this method, a quantity of the secondary amine is mixed with a 2x molar ratio of the dioxirane. In a first reaction, the secondary amine is oxidized to form a hydroxylamine; in a second reaction, the hydroxylamine is further oxidized to form a nitroxide. When the dioxirane compound loses an oxygen atom it converts into a ketone; for example, dimethyldioxirane is converted into acetone, while methylethyldioxirane is converted into methylethylketone. This is very convenient, since the ketone byproduct is a solvent that can be easily controlled during the reaction and easily removed after the reaction without causing interfering reactions. This method provides a simple, highly selective, rapid reaction with very high yields. It can be carried out in a single reaction vessel and can be used with a wide variety of secondary amines to create a corresponding variety of nitroxides.

DETAILED DESCRIPTION OF THE PREFERRED EMBODIMENTS

Figure 1:
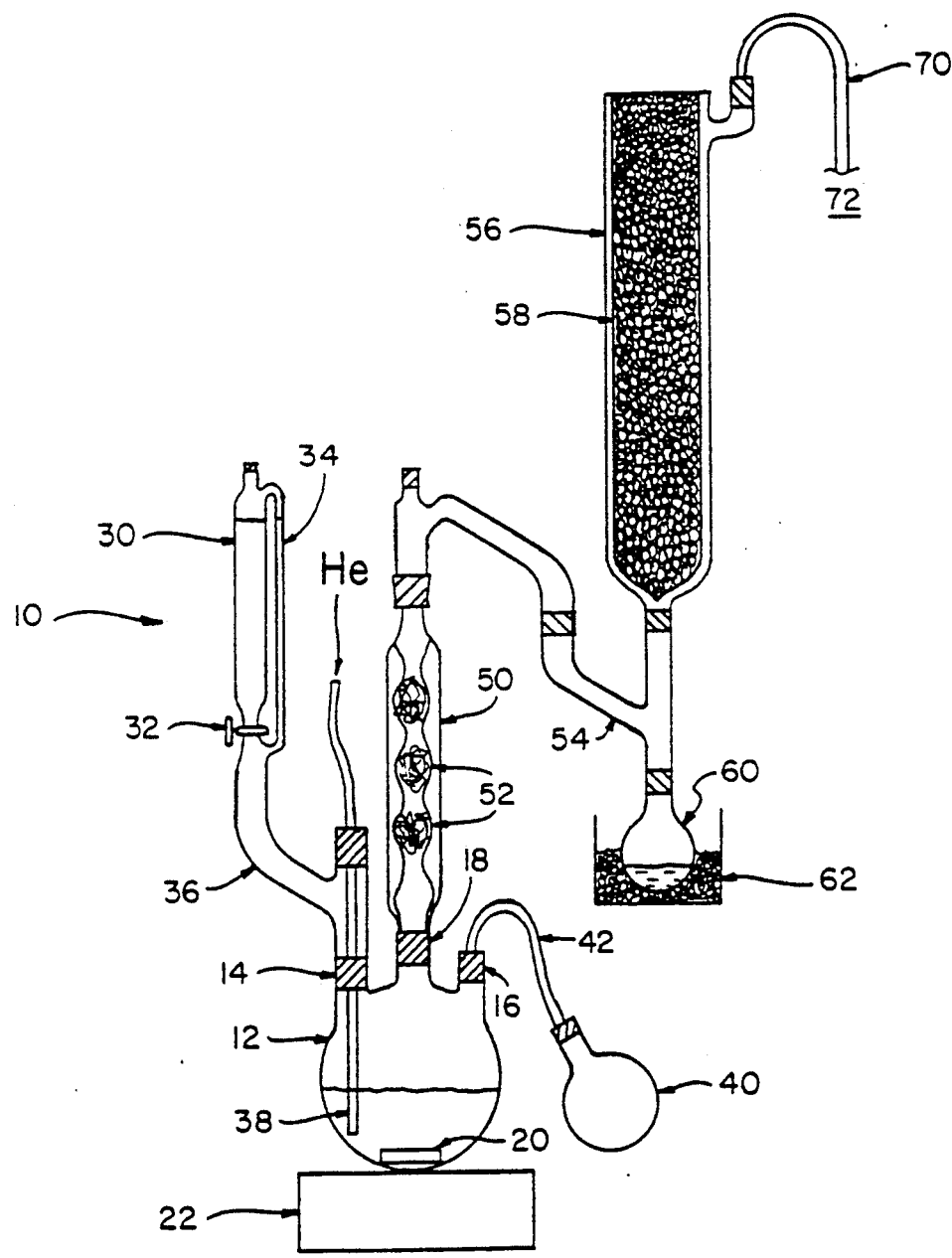
FIG. 1 depicts the reaction vessels used to synthesize dimethyldioxirane.

The subject invention involves the use of dioxirane compounds to convert secondary amines to their corresponding nitroxides. The specific dioxirane derivative used in the Examples is dimethyldioxirane (DMD). That particular derivative is used because (1) it is relatively simple and inexpensive to synthesize, (2) it is sufficiently stable for use in the subject invention, and (3) DMD yields a preferred solvent, acetone, rather than an undesired byproduct when it loses an oxygen atom.

If desired, other dioxirane derivatives (such as methylethyldioxirane or halogenated dioxiranes) can be synthesized and used instead of dimethyldioxirane to convert secondary amines into nitroxides. Unless such other dioxirane derivatives are deliberately provided with highly reactive groups at other locations on the molecule, which might cause competing reactions, the dioxirane structure will react quickly and selectively with secondary amine groups on the reagents to form nitroxides.

Secondary amines suitable for use in this invention should not have hydrogen bonded to either of the "alpha" carbons (i.e., the carbon atoms that are directly bonded to the nitrogen). If a hydrogen atom is bonded to either of the alpha carbons, the resulting nitroxide is prone to spontaneous degeneration and is usually converted into a nitrone. Suitable secondary amines for use as described herein have the following general formulas:

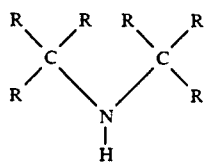

wherein each R can be any group other than hydrogen. Preferred R's include alkyl groups, aryl groups, cycloalkyl groups, oxygen-containing groups such as methoxy, and halogen atoms such as fluorine, chlorine, and bromine.

Table 1 summarizes the yields of several reactions described in the Examples.

The equipment assembly 10 for creating the dimethyldioxirane used to carry out the method of this invention is shown in FIG. 1. The reaction vessel comprises a three-necked flask 12, wherein the three necks serve as inlets 14 and 16 and outlet 18. A magnetic stirring bar 20 is placed in the reaction vessel 12; it is rotated by a magnetic stirrer 22.

The reaction vessel 12 is initially charged with a mixture of acetone, water, and sodium bicarbonate. It is kept at room temperature during the DMD synthesis.

TABLE 1

| YIELDS OF VARIOUS NITROXIDES | |
|---|---|
| Nitroxide | Yield (%) |
| 2,2,6,6-tetramethyl-4-piperidinol-1-yloxy | 100 |
| 2,2,6,6-tetramethyl-4-piperidone-1-yloxy | 98 |
| 2,2,6,6-tetramethyl piperidone-4-oxime-1-yloxy | 99 |
| 3-carbamoyl-2,2,5,5-tetramethyl-3-pyrroline-1-yloxy | 98 |
| 3-carboxy-2,2,5,5-tetramethyl-3-pyrroline-1-yloxy | 94 |
| 3-carboxy-2,2,5,5-tetramethyl-3-pyrrolidine-1-yloxy | 98 |
| 3-carbamoyl-2,2,5,5-tetramethyl pyrrolidine-1-yloxy | 100 |
| 4-ethynyl-4-hydroxy-2,2,6,6-tetramethylpiperidine-1-oxyl | 80 |
| 3,3-dimethyl-1-oxa-4-azaspiro[4.5]dec-4-yloxy | 100 |
| 4',4'-dimethylspiro(5α-cholestane-3,2'-oxazolidine)-3'yloxy | 97 |
| ditertiarybutylnitroxide | 86 |

A liquid addition unit 30 with a stopcock 32 and a pressure equalizer 34 is coupled to inlet 14 of reaction vessel 12 via a Y-tube 36. A continuous supply of gaseous helium (an inert gas used as a carrier for the gaseous DMD) is provided to reaction vessel 12 via the other inlet provided by Y-tube 36. The helium is injected into the bottom region of reaction vessel 12 via tube 38. The inert carrier gas should be injected below the surface of the liquid, and can be dispersed throughout the reaction vessel by a dispersing nozzle or manifold on the bottom of the vessel. Second inlet 16 of reaction vessel 12 is coupled to a vessel 40 which contains Oxone (a trademark of DuPont), a formulation containing monoperoxysulfuric acid, $2KHSO_5.KHSO_4.K_2SO_4$. The vessels are coupled via a device such as a flexible tube 42 which allows the Oxone (in granular form) to be added slowly to reaction vessel 12.

Outlet 18 of reaction vessel 12 is coupled to vapor column 50, which is packed with glass wool 52 to prevent any liquid from the reaction vessel 12 from spattering into the receiving flask. Vapors (which contain DMD and acetone) from the reaction vessel are carried through the glass wool 52 with the aid of the helium carrier gas. Those vapors enter Y-tube 54, which is connected to condensation unit 56. The interior chamber 58 of condensation unit 56 contains a very cold mixture such as dry ice and acetone. As the vapor which contains DMD contacts the cold surfaces in condensation unit 56, it condenses. The yellow condensate collects in the main receiving flask 60, via Y-tube 54. The condensate chills the Y-tube 54 and the receiving flask 60, causing some of the vapors to condense directly into the receiving flask. The receiving flask is also chilled directly, by means such as dry ice-acetone bath 62.

Any vapors which are still in gaseous form after they pass through the condensation unit 56 can be collected via tube 70 in one or more cold traps 72 if desired. The applicants have found that a single trap containing dry ice and acetone is sufficient to collect the large majority of any remaining DMD. In industrial processes, it may be advisable to provide additional cold traps to ensure complete removal of any DMD.

The DMD/acetone mixture collected in receiving flask 60 and in any cold traps can be stored in a conventional freezer (at 0° C. or slightly colder temperatures) for up to about seven days with little or no degradation. If storage for more than a few days is required, the concentration of the DMD should be assayed shortly before it is used.

The concentration of DMD in acetone solution can be assayed by various methods. In the work described in the Examples, the DMD concentrations were determined by the phenyl methyl sulfide method (Murray et al 1985). Other methods include a triphenylphosphine method (Murray et al 1985), UV spectroscopy (absorbance at 331-335 nm), and iodometric titration.

The addition of 2x DMD (i.e., 2 moles of DMD per mole of secondary amine) leads to a sequence of two reactions. In the first reaction, the secondary amine is converted into a hydroxylamine. That oxidation reaction is rapid and highly selective, as indicated by the fact that if only equimolar DMD is added, relatively pure hydroxylamine is obtained. After the secondary amine reagent is depleted, the remaining DMD becomes highly selective for the hydroxylamine groups, in preference to other potentially reactive groups. This leads to high yields of relatively pure nitroxides, as indicated in Table 1. Alternately, if complete conversion of a secondary amine to a nitroxide is not desired, a lesser quantity of dioxirane can be provided.

All of the nitroxides described in the Examples were tested via ESR, using benzene solvent ($10^{-3}$M). All showed the characteristic three-line nitroxide spectrum with g and $a_N$ values as described in Rozantsev et al 1971.

As shown in the Examples, the method of this invention has been performed on a variety of secondary amines which have reactive groups that were not altered by the dimethyldioxirane. Such potentially reactive groups which have been tested and found not to interfere with or be affected by the dioxirane-amine reaction described herein include secondary alcohols, bicyclic groups with spiro configurations (i.e., the adjoining rings share a single carbon atom), aromatic rings, heterocyclic rings containing oxygen atoms, an unsaturated ring having a double bond, a side group with triple bonded carbons, carboxamide groups, carboxylic acid groups, a ketone, and an oxime. Thus, this reaction has been shown to be highly selective for secondary amine groups, despite the presence of various different types of potentially competing reactive groups.

This invention is not limited to the conversion of soluble amines into soluble nitroxides; instead, it can also be used to convert at least some insoluble amines into nitroxides. For example, Examples 5 and 6 disclose the conversion of two insoluble secondary amines into soluble nitroxides. Both types of amines, in small particulate form, were suspended in solution by stirring. In both cases, the conversion proceeded at sufficient rates to drive each reaction to completion, dissolving all of the amine particles and converting them into soluble nitroxides within an hour. In addition, Example 10 discloses the conversion of a soluble amine into an insoluble hydroxylamine intermediate, followed by the conversion of the insoluble hydroxylamine into a soluble nitroxide.

In general, nitroxides tend to be relatively soluble in a wide variety of organic solvents, due to the stabilized free radical electron on the oxygen atom. Therefore, if a secondary amine with no alpha hydrogens has limited solubility in acetone, or in a mixture of acetone (or some other ketone) and a second solvent such as methylene chloride, the reaction can still proceed, as shown by Examples 5, 6, and 10.

Based on the results obtained to date, it is believed that the method disclosed herein can also convert at least some of the amine groups in insoluble or partially soluble secondary amines (such as polymeric secondary amines or other secondary amines with very high molecular weights) into nitroxide groups. In such reactions, the preferred mode of reaction would involve suspending small particles of the insoluble amine in a stirred liquid solution containing dioxirane.

This process has also been shown to work successfully and with high efficiency on a secondary amine having more than one amine group; the detailed data and results are provided in Example 12. In that particular compound, both of the two amine groups on the starting compound were completely converted into nitroxide groups. This result demonstrates two things: (1) in compounds having more than one secondary amine group with no alpha hydrogens, at least one of the amine groups will be converted into a nitroxide group; and, (2) in at least some compounds having more than one secondary amine group with no alpha hydrogens, more than one and possibly all of the amine groups will be converted into nitroxide groups.

The preferred solvents for use with specific secondary amine compounds may vary between different amines. In general, if an amine is soluble in a particular solvent at the preferred temperatures, then the reaction will proceed more quickly than if the amine is insoluble. Therefore, if a certain secondary amine is insoluble in acetone and other ketone solvents but is soluble in another selected solvent, the amine can be dissolved in the other selected solvent, and the resulting mixture can be mixed with the dioxirane solution in acetone (or another ketone).

In some cases, the addition of a second solvent may increase the speed or the yield of the desired reaction. For example, a series of epoxidation experiments were carried out involving olefins and dimethyldioxirane. These experiments are not directly related to the conversion of secondary amine groups to nitroxides; instead, they involve the following reaction:

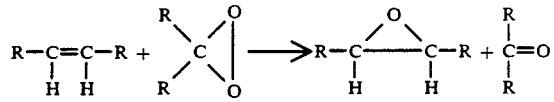

However, during those experiments it was discovered that the incorporation of methylene chloride ($CH_2Cl_2$) in the solvent mixture increased the rate of epoxidation. Based on theoretical considerations, it is suspected that in some situations, the addition of methylene chloride or other solvents to the solvent mixture might also increase the rate of reaction of certain amine-to-nitroxide conversions. An example of a secondary amine being converted to a nitroxide in a mixed solvent comprising acetone and methylene chloride is provided in Example 13.

In general, one of the advantages of the method of this invention when used with most secondary amines is that it can be carried out in acetone solution (or in some other ketone solvent, if a dioxirane other than dimethyldioxirane is used). That is advantageous because the dioxirane will be converted into the ketone solvent when it donates an oxygen atom to the amine. After the reaction is complete and it is time to purify the resulting nitroxide, it is necessary to remove (and handle, to avoid atmospheric escape of) only one type of solvent, which can be done quite easily by methods such as vacuum distillation. By contrast, if two different solvents are used, then both must be removed (which may require two different procedures and special types of handling for environmental and personnel safety).

However, in some situations involving certain secondary amines that are not soluble in acetone or other ketones, that advantage might be outweighed by the need to use an additional solvent in order to increase the solubility of the amine, thereby increasing the rate of reaction between the dioxirane and the amine. In such cases, any desired type of solvent may be used if it increases the solubility if any specific amine; candidate solvents can include highly polar, moderately polar, or non-polar solvents, as well as protic solvents. For most amines, the proper selection of a second solvent will be fairly apparent to any chemist skilled in the art of organic chemistry, based on the characteristics of the amine molecule. In cases where the proper choice is not obvious, the person carrying out the reaction can test various different types of solvents in a screening process which would involve steps such as identifying a solvent in which the amine is soluble and preparing a mixture of the solvent and the amine, then adding acetone to the mixture to determine whether the acetone causes precipitation or immiscibility. If the mixture remains soluble, then the dioxirane reaction should proceed as described herein. However, even if some precipitation or immiscibility occurs, the amine groups can still be converted to nitroxides, as evidenced by Examples 5, 6, and 10.

The optimal temperature for carrying out the conversion of any specific type of secondary amine can be determined through routine experimentation. In general, temperatures in the range of about −20° to about +10° C. are preferred for most conversions, because such temperatures can be achieved quite easily and inexpensively through the use of ice baths; however, temperatures outside that range can be used for specific conversions if desired, and the optimal temperature for any specific reaction will often depend on economic considerations rather than purely chemical considerations. In general, the O—O bond in dioxirane, like the O—O bond in any other type of peroxide, is labile; as temperatures increase above the freezing range and approach the range of room temperatures, that O—O bond is more likely to break, leading to highly reactive oxygen free radicals that can cause undesired, non-specific competing reactions. At the other end of the temperature range, as reaction conditions become colder, the reaction proceeds more slowly. Therefore, it is generally desirable to carry out reactions at the highest temperature which does not lead to undesired competing reactions. In view of the fact that many peroxide reactions will not proceed at any appreciable rate at freezing temperatures, the discovery that the dioxirane reaction disclosed herein does indeed proceed quickly, at very high yields, and with very high selectivity at freezing temperatures was quite unexpected.

EXAMPLES

Reagents

Acetone (Fisher Chemicals, Fair Lawn NJ), was fractionally distilled over anhydrous potassium carbonate. Benzene (Fisher), petroleum ether (Fisher), diethyl ether (Fisher), ligroin (MCB, Norwood Ohio) cyclohexanone (Aldrich) and 2-amino-2-methyl-1-propanol (Aldrich) all were of highest commercial purity and were purified by distillation before use. 5-α-cholestane-3-one and 2-amino-2-methyl-1-propanol were obtained from Aldrich (Milwaukee Wis.) and were of highest commercial purity. N-tert-butyl-N-benzylamine (Aldrich), N,N-dibenzylamine (Aldrich), N,N-diisobutylamine (Aldrich), N,N-dicyclohexylamine (Kodak, Rochester, N.Y.) were fractionally distilled under reduced pressure before use. Oxone (DuPont), $2KHSO_5 \cdot KHSO_4 \cdot K_2SO_4$ was obtained from Aldrich and used without further purification. Anhydrous $K_2CO_3$ (Aldrich), hydroxylamine hydrochloride (Mallinckrodt, St. Louis), anhydrous sodium sulfate (Aldrich), sodium borohydride (Ventron, Beverly, Mass.), barium hydroxide octahydrate (Aldrich), and anhydrous magnesium sulfate (Fisher) were used without further purification.

All boiling points (bp), melting points (mp), and other temperatures are expressed in degrees Celsius. Unless otherwise specified, "cold" solutions were kept in ice baths at approximately 0° C. All stirring was done using magnetic stirring bars (although mechanical stirring could be used if desired), and all mixing of solutions was done dropwise.

Synthesis and Storage of DMD

Acetone solutions containing dimethyldioxirane (DMD) were prepared by the method of Murray et al 1985, scaled up as follows and using only one cold trap instead of five. A 2000 ml 3-necked round bottom flask containing a mixture of water (80 ml), acetone (50 ml, 0.68 mol) $NaHCO_3$ (96 g), and a stirring bar was coupled via a rubber tube to a flask containing granular Oxone (180 g, 0.29 mol). A pressure-equalized dropping funnel containing water (60 ml) and acetone (60 ml, 0.82 mol) was coupled to another neck of the flask, via a Y-tube as shown in FIG. 1. A vapor column, loosely packed with glass wool, was attached to the third neck of the reaction vessel.

The outlet of the air condenser was connected to an acetone-dry ice condenser, which was attached to a receiving flask (100 ml) cooled in an acetone-dry ice bath. The receiving flask was connected to a dry ice-acetone cold trap.

Helium was bubbled through the reaction mixture while the granular Oxone was added in small portions by lifting the Oxone flask. The acetone-water mixture was added simultaneously, dropwise. The mixture was stirred vigorously at room temperature throughout the reaction period. After 15 min of reaction time, a slight vacuum was applied to the reaction assembly using a water aspirator.

The yellow-colored DMD-acetone solution collected primarily in the receiving flask; some material was found in the cold trap. The two solutions were mixed, stirred briefly with sodium sulfate to remove part of the water, filtered, and stored at 0° to −5° for up to about seven days.

Solutions were assayed for DMD content using phenyl methyl sulfide. The concentrations were in the range of 0.04 to 0.185M. Quantities of solution added to secondary amine reagents were varied accordingly, to achieve 2:1 (DMD:amine) molar ratios.

Analytical Instrumentation $^1H$ and $^{13}C$ NMR data were obtained in $CDCl_3$ solution at 300 MHz and 75 MHz, respectively, on a Varian XL-300 fourier transform spectrometer. $^1H$ NMR spectra used the 7.24 ppm resonance of residual chloroform as an internal standard; $^{13}C$ NMR spectra used the $CDCl_3$ resonance at 77.00 ppm as an internal standard. In both $^1H$ NMR and $^{13}C$ NMR chemical shifts are reported in δ units downfield from tetramethylsilane. Infrared spectra were recorded on a Perkin-Elmer model 783 grating spectrophotometer in KBr pellets. ESR spectra were recorded at X-band with a Varian E-12 spectrometer equipped with a dual cavity using experimental and analytical techniques described in Jones et al 1973. Nitroxide solutions ($10^{-3}$M) were thoroughly degassed by the "freeze-pump-thaw" method on a high vacuum line.

Mass spectra were recorded on either a Finnigan 4500 twin EI and CI quadrupole mass spectrometer or on an Associated Electronics Industries model MS-1201B mass spectrometer at 70 eV unless otherwise noted, with pertinent peaks reported as m/e (relative intensity). GC-Mass spectra were recorded on either a Hewlett-Packard 5992 model gas chromatograph-mass spectrometer (DB-5 Megabore column), where the peak finder program was used for product analysis and the SIM (selected ion monitoring) program was used for obtaining ion ratios, or on a Hewlett-Packard 5988A twin EI and CI quadrupole mass spectrometer at 70 eV by a direct probe. GC-Mass spectra were recorded on the HP 5988A model instrument using a gas chromatograph (HP-1 column, 15 meters). Melting points were measured on either a Dynamics optics AHT 713921 hot-stage apparatus or on a Thomas-Hoover capillary melting point apparatus and are uncorrected. The notation "dec." indicates that the compound was degraded upon melting. Usually this was indicated by a color change; in several cases, it was confirmed that the substance would not recrystallize upon cooling.

Example 1: 2,2,6,6-tetramethyl-4-piperidinol-1-yloxy 2,2,6,6-tetramethyl-4-piperidinol was prepared by the reduction of 2,2,6,6-tetramethyl-4-piperidone (Aldrich) with sodium borohydride. It was purified by recrystallization from ligroin (bp 65–90). It formed colorless needles with mp 130–131; the reported mp is 128–131 (Lutz et al 1962).

A solution of 0.067M dimethyldioxirane in acetone (30 ml, 2 mmol) was added to a cold stirred solution of the prepared 2,2,6,6-tetramethyl-4-piperidinol (157 mg, 1 mmol) in acetone (10 ml). The reaction mixture, which became orange yellow in 5-10 minutes, was stirred for 2 hours. The solvent was evaporated on a rotary evaporator to give an orange solid (173 mg, 100% yield). Sublimation of the solid at $10^{-3}$ torr gave orange colored needles. Measured mp was 71–72; reported mp 70–71 (Rozantsev 1970). This nitroxide has the following structure:

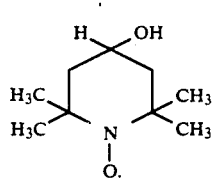

Example 2: 2,2,6,6-tetramethyl-4-piperidone-1-yloxy

A solution of 0.066M DMD in acetone (61 ml, 4 mmol) was slowly added to a cold stirred solution of 2,2,6,6-tetramethyl-4-piperidone monohydrate (Aldrich; 352 mg, 2 mmol) in acetone (10 ml). The reaction mixture, which became yellow orange in 10-15 minutes, was stirred for 2 hours. The solvent was evaporated on a rotary evaporator to give an orange pasty solid. The pasty solid was extracted twice with diethyl ether and the combined ether extracts were dried with anhydrous magnesium sulfate and evaporated to afford a pinkish orange solid (341 mg, 98%). Measured mp was 33-34; reported mp is 36 (Rozantsev 1970).

The structure of this nitroxide is as follows:

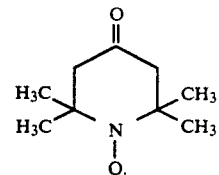

Example 3: 2,2,6,6-tetramethyl piperidone-4-oxime-1-yloxy 2,2,6,6-tetramethyl piperidone-4-oxime was prepared by the reaction of hydroxylamine hydrochloride with 2,2,6,6-tetramethyl-4-piperidone (Aldrich). Free oxime was obtained by the addition of potassium hydroxide to an aqueous solution of hydrochloride and several diethyl ether extractions. The extract was dried over anhydrous Na$_2$SO$_4$ and evaporated to give a crystalline solid which was recrystallized (forming colorless plates) from a mixture of diethyl ether and petroleum ether. The measured mp was 154–155; the reported mp is 155 (Briere et al 1965).

A solution of 0.066M DMD in acetone (16 ml, 1.05 mmol) was slowly added to a cold stirred solution of 2,2,6,6-tetramethyl piperidone-4-oxime (85 mg, 0.5 mmol) in acetone (5 ml). The reaction mixture, which became orange in 5 minutes, was stirred for 2 hours. The solvent was evaporated on a rotary evaporator to give an orange red crystalline solid (92 mg; 99%). Measured mp was 180-185; reported mp is 180 (Rozantsev 1970)

The structure of this nitroxide is as follows:

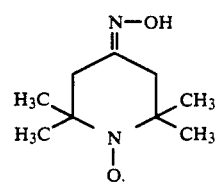

Example 4: 3-carbamoyl-2,2,5,5-tetramethyl-3-pyrroline-1-yloxy 2,2,5,5-tetramethyl-3-pyrroline-3-carboxamide (Frinton; Vineland, N.J.) was dissolved in hot benzene and recrystallized to purify it. The measured mp was 180–181.

A solution of 0.055M DMD in acetone (18.5 ml, 1.01 mmol) was slowly added to a cold stirred solution of 2,2,5,5-tetramethyl-3-pyrroline-3-carboxamide (84 mg, 0.5 mmol; Frinton, Vineland, N.J.; recrystallized from benzene) in acetone (10 ml). The reaction mixture, which became yellow in 10–15 minutes, was stirred for 2 hours. The solvent was evaporated on a rotary evaporator and the residue was dissolved in acetone and filtered. The filtrate was concentrated on a rotary evaporator to give bright yellow needles (89 mg, 98%). The measured mp was 203–204 (dec.; chloroform-hexane); the reported mp 203–204 dec. (Rozantsev et al 1965a).

The nitroxide has the following structure:

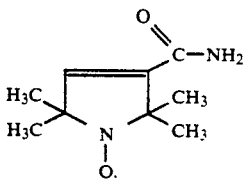

Example 5:
3-carboxy-2,2,5,5-tetramethyl-3-pyrroline-1-yloxy 2,2,5,5-tetramethyl pyrroline-3-carboxylic acid was prepared by the hydrolysis of 2,2,5,5-tetramethyl pyrroline-3-carboxamide (Frinton; recrystallized from benzene) with barium hydroxide. The acid was recrystalized from water to provide an off-white solid. The measured mp was 300 (dec.) in a sealed tube; the reported mp was 300 dec. (Pauly 1902; Rozantsev 1970).

A solution of 0.055M DMD in acetone (36.7 ml, 2 mmol was slowly added to a cold stirred homogeneous suspension of 2,2,5,5,-tetramethyl-3-pyrroline-3-carboxylic acid (205 mg, 1 mmol) in 5 ml of acetone (i.e., small particles of the insoluble amine, which has a carboxylic acid group elsewhere on the molecule, were suspended in stirred acetone). The reaction mixture, which became clear yellow in 1 hour, was stirred for 3 hours. The solvent was evaporated on a rotary evaporator to give a yellow microcrystalline solid, which was dissolved in benzene and filtered. Evaporation of the solvent afforded fine yellow needles (210 mg, 94%). Measured mp was 210–215 dec.; reported mp is 210–211 dec. (Rozantsev et al 1965a).

The structure of this nitroxide is as follows:

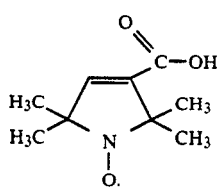

Example 6:
3-carboxy-2,2,5,5-tetramethyl-3-pyrrolidine-1-yloxy 2,2,5,5-tetramethyl-3-pyrrolodine-3-carboxylic acid monohydrate was prepared by hydrolyzing the carboxamide (Frinton) with barium hydroxide. The mp was 220, which agreed with Pauly 1902. A solution of 0.041M DMD in acetone (24.38 ml, 1 mmol) was slowly added to a cold stirred suspension of 2,2,5,5-tetramethyl-3-pyrrolodine-3-carboxylic acid monohydrate (0.0946 g, 0.5 mmol) in acetone (10 ml). The reaction mixture, which became clear yellow in 1 h, was stirred for 2.5 h at 0° C. The solvent was removed on a rotary evaporator to give a bright yellow crystalline solid (0.0936 g). The solid was dissolved in CHCl₃, and the solvent was removed, after drying with anhydrous Na₂SO₄, to give a chromatographically homogeneous yellow crystalline solid (0.0920 g, yield 98%). The measured mp was 200–202 dec. (sublimation occurred at 150–160); the reported mp is 200 dec. (Rozantsev et al 1965a).

The structure of this nitroxide is as follows:

IR (KBr,cm⁻¹): 3450(br), 3200–2900(br), 2990, 1735(C=O), 1465, 1422, 1410, 1385, 1375, 1305, 1260, 1250, 1200, 1170, 1150, 1110, 1070, 900(br), 672.

Example 7: 3-carbamoyl-2,2,5,5-tetramethyl pyrrolidine-1-yloxy

A solution of 0.067M DMD in acetone (60 ml, 4 mmol) was added slowly to a cold stirred solution of 2,2,5,5-tetramethyl pyrrolidine-3-carboxamide (340 mg, 2 mmol; Frinton, recrystallized from benzene, mp 130) in acetone (20 ml). The reaction mixture, which became yellow in 10 minutes, was stirred for 2 hours. The solvent was evaporated on a rotary evaporator to give a bright yellow crystalline solid (370 mg, 100%). When recrystallized from hot acetone, bright yellow needles were created. The measured mp was 174–176; the reported mp is 174–174.5 (Rozantsev et al 1965a).

This nitroxide has the following structure:

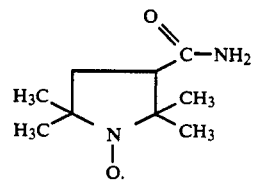

Example 8: 4-ethynyl-4-hydroxy-2,2,6,6-tetramethylpiperidine-1-oxyl

A solution of 0.041M DMD (924.4 ml, 1 mmol) was slowly added to a cold stirred suspension of 4-ethynyl-4-hydroxy-2,2,6,6-tetramethylpiperidine (0.09063 g, 0.5 mmol, prepared by the method of Lutz et al 1962) in acetone (10 ml). The reaction mixture was stirred for 1 hour in an ice bath. The resulting orange solution was stripped of solvent to give an orange crystalline solid (0.09715 g), which was purified by flash chromatography on silica gel with 30:70 ethyl acetone/petroleum ether elution to provide analytically pure orange crystalline solid (0.0790 g, yield 80.5%). The measured mp was 119–120; the reported mp is 119.5 (Litvin et al, 1979).

The structure of this nitroxide is as follows:

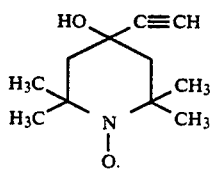

IR (KBr,cm⁻¹): 3350(br, OH), 3235(s, C—H), 2110(w,—C CH), 1470, 1460, 1400, 1385, 1370(N—O°), 1341, 1300, 1245, 1205, 1178, 1040, 920, 720, 700, 570.
MS(m/e): 197 (M+1), 196 (M+).

Example 9: 3,3-dimethyl-1-oxa-4-azaspiro [4.5]dec-4-yloxy

Oxazolidines were synthesized by the procedures of Hancock 1944 and Keana 1967, and were purified by fractional distillation under reduced pressure. The 3,3-dimethyl-1-oxa-4-azaspiro-[4.5]decane had a measured bp 98-99 at 20 mmHg; the reported bp was 95-97.5 at 20 mmHg (Hancock 1944).

A solution of 0.055M DMD in acetone (29.6 ml, 1.62 mmol) was slowly added to a coldsstirred solution of 3,3-dimethyl-1-oxa-4-azaspiro [4.5] decane (137 mg, 0.81 mmol) in acetone (5 ml). The reaction mixture, which became yellow in 5 minutes and dark yellow in 15 minutes, was stirred for 1.5 hours. The solvent was evaporated on a rotary evaporator to give an orange oil emulsified with water. Addition of anhydrous potassium carbonate (1 g) to the suspension gave an orange-yellow crystalline solid. The solid was extracted twice with diethyl ether and the combined ether extracts were dried with anhydrous sodium sulfate and evaporated to afford an orange crystalline solid (149 mg, 100%) which was further purified by sublimation at room temperature, at $10^{-3}$ torr. The final product was in the form of orange-yellow cubes. The measured mp was 61-62; the reported mp is 57-59 (Keana et al 1967).

This nitroxide has the following structure:

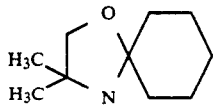

Example 10: 4',4'-dimethylspiro(5α-cholestane-3,2'-oxazolidine)-3'yloxy 4,4'-dimethylspiro(5α-cholestane-3,2'-oxazolidine) was prepared by the method of Keana et al 1967. Briefly, a solution of 5α-cholestane-3-one (Aldrich; 1.53 g, 3.95 mmol), 2-amino-2-methyl-1-propanol (1 ml, excess 10.47 mmol), dry toluene (60 ml), and p-toluene sulfonic acid monohydrate (0.050 g) was refluxed for 60 hours with continuous water removal by means of a Dean-Stark trap. Toluene was washed with 100 ml of a saturated NaHCO₃ brine solution (4×50 ml) and water (4×50 ml). The washed toluene layer was dried with anhydrous Na₂SO₄. The toluene was removed on a rotary evaporator to give a white microcrystalline solid (1.8 g). The measured mp was 120-125; the reported mp Was 124-125 (Keana et al 1967).

A solution of 0.047M DMD in acetone (21.26 ml, 1 mmol) was added to a cold solution of 4',4'-dimethyl-spiro(5α-cholestane-3,2'-oxazolidine) (0.2289 g, 0.5 mmol) in acetone (10 ml). A white solid began to form due to the formation of intermediate hydroxylamine, but after a few minutes the reaction mixture became yellow. The yellow reaction mixture was stirred at 0° C. for another 3 hours. The solvent was evaporated on a rotary evaporator to afford a yellow crystalline solid (0.2315 g). The yellow solid was dissolved in acetone, filtered, and evaporated to afford a chromatographically pure, yellow crystalline solid (0.2301 g, 97% yield). The measured mp was 178-181; the reported mp is 176-177 (Keana et al 1967).

This nitroxide has the following structure:

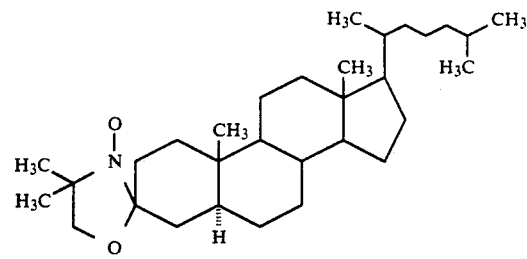

IR (KBr,cm$^{-1}$): 2960, 2930, 2860, 1470, 1465, 1455, 1430, 1385, 1378(N—O°), 1365, 1300, 1285, 1265, 1050, 960, 935, 825. ESR (CHCl₃) superposable with esr spectrum of equatorial isomer of 4',4'-dimethylspiro(5α-cholestane-3,2'-oxazolidine)-3'-yloxy (Marriott et al 1976).

Example 11: Di-tertiary-butylnitroxide

In order to prove that the method of this invention can convert secondary amines having branched alkyl groups attached to the nitrogen atom, di-tertiary-butylamine was converted into di-tertiary-butylnitroxide.

Since di-tertiary-butylamine is not commercially available, it was generated by hydrogenating di-tertiary-butylnitroxide (Lancaster Synthesis, Windham, N.H.) in the presence of Raney Nickel catalyst in ethanol, using the method of Rozantsev et al 1968. The resulting amine was converted into an oxalate salt by addition of oxalic acid; since the nitroxide cannot be converted into the oxalate salt, this effectively separated the amine from any unreacted nitroxide. The oxalate salt was precipitated out, filtered, and mixed with NaOH to convert it into the amine. The amine was extracted with ether, the ether was evaporated, and the amine was distilled at about 117° C. at 735 torr to isolate pure amine.

A solution of 0.065M DMD in acetone (34 ml, 2.2 mmol) was added to a cold (0° C.) solution of di-tertiary-butylamine (0.1419 g, 1.1 mmol) in acetone (5 ml). A yellow-orange color appeared, and the mixture became light orange-red within a few minutes. The mixture was stirred at 0° for 1 hour. The acetone was removed by distillation. The residue was a red oil with traces of water. The water was removed by dissolving the mixture in pentane, adding a drying agent (MgSO₄) which absorbed the water, removing the hydrated drying agent, and evaporating the pentane. The resulting product was a chromatographically pure, bright red oil with a strong camphor-like odor (0.137 g, 86.5% yield).

This nitroxide has the following structure:

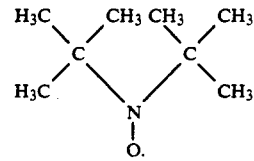

Example 12: Bis(1-oxyl-2,2,6,6-tetramethyl-4-piperidyl)decanedioate

An industrial grade sample of bis(2,2,6,6-tetramethyl-4-piperidyl)decanedioate (CAS number 52829-07-09) was obtained from Ciba-Geigy (Ardsley, N.Y.). This molecule contains two secondary amine groups with no alpha hydrogens, separated by an organic linkage as indicated in the structure shown below. One mmol (0.48072 g) was dissolved in 10 ml acetone in a magnetically stirred ice bath, and 4 mmol (68 ml of 0.059M) DMD was added. The reaction mixture quickly turned orange, and was stirred for 1 hr at 0° C. The solvent was removed on a rotary evaporator to give an orange-red crystalline solid. The weight of the crystalline solid (0.5209 g) was slightly higher than the theoretical yield, indicating that not all of the solvent had been removed. The measured melting point was 101-104; reported mp is 101 (Rozantsev et al, 1965b).

IR(KBr, cm$^{-1}$): 2973, 2933, 2852, 1732 (C=O), 1467, 1377, 1348, 1276, 1241, 1174, 1125, 1089, 985, 962, 939, 920, 728, 682, 562.

Mass(EI, 70 eV): m/z 511 (M+1, 1.4), 510 (M+, 2.9), 356 (9.3), 154 (40.7), 124 (base peak), 109 (60). The calculated molecular weight for $C_{28}H_{50}N_2O_6$ is 510.70, which is in agreement with the mass spectroscopy result of 510.

ESR of the polycrystalline solid: single line (LW=12.5 G); the g value at the center of the line was 2.006384.

ESR of the solid dissolved in CHCl$_3$: three line hyperfine splitting at $a_N$=15.7 G; g value was 2.006177.

This di-nitroxide has the following structure:

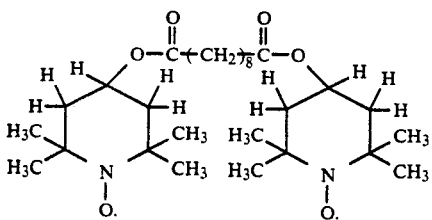

Example 13: Dichloromethane/acetone solvent

To evaluate the dioxirane reaction in a mixed solvent, the nitroxide compound described in Example 4 (3-carboxy-2,2,5,5-tetramethyl-3-pyrroline-1-yloxy) was synthesized in a solvent containing both dichloromethane (also called methylene chloride) and acetone.

The same starting amine (2,2,5,5-tetramethyl-3-pyrroline-3-carboxamide) that was described in Example 4 was used. It was dissolved in hot benzene and recrystallized to purify it; 0.051 g (0.3 mmol) was dissolved in 5 ml of dichloromethane and chilled in a magnetically stirred ice bath. A solution of 0.049 mole DMD in acetone (12.4 ml, 0.6 mmol) was diluted with an equal volume of dichloromethane (12.4 ml), and added to the amine mixture. The reaction mixture became clear yellow in about 5 to 10 minutes; by contrast, when dichloromethane was not present and acetone was the only solvent present, the same reaction took longer (about 10 to 15 minutes). The mixture was stirred for 1 hour at 0° C., then the solvent was removed on a rotary evaporator to give a bright yellow crystalline solid. The solid was dissolved in acetone, the mixture was dried with anhydrous Na$_2$SO$_4$, and the acetone was removed to give a chromatographically homogenous yellow crystalline solid (0.0548 g; yield 98.6%). The measured melting point was 202°-203° C.; the reported melting point is 203°-204° C. (Rozantsev et al 1965a).

This nitroxide has the structure shown in Example 4.

REFERENCES

Berliner, J. L., Ed., *Spin Labelling, Theory and Applications*, Academic Press, New York, 1976

Briere, R., et al, *Bull. Soc. Chim. Fra.* 1965: 3273, 1965

Eaton, P. E., et al, *J. Org. Chem.* 53: 5353, 1988

Hancock, E. M., et al, *J. Am. Chem. Soc.* 66: 1738, 1944

Holtzman, J. L., Ed., *Spin Labelling in Pharmacology*, Academic Press, N.Y., 1984

Jones, M. T., et al *J. Phys. Chem.* 83: 1327, 1973

Keana, J. F. W., et al, *physiolog. Chem. Phys. Med. NMR* 17: 235, 1985

Keana, J. F. W., et al, *J. Am. Chem. Soc.* 89: 3055, 1967

Klemchuk, P. P., Ed., *Polymer Stabilization and Degradation*, ACS Symposium Volume No. 280, 1985

Litvin, E. F., et al, *Izv. Akad. Nauk. SSSR, Ser. Khim.:* 109 (1979), *Chem. Abstr.* 90: 203825d, 1979

Lutz, W. B., et al, *J. Org. Chem.* 27: 1695, 1962

Marriott, T. B., et al, *J. Mag. Reson.*24: 41 (1976)

Mello, R., et al, *J. Org. Chem.* 53: 3890, 1988

Murray, R. W., et al, *J. Org. Chem.* 50: 2847, 1985

Murray, R. W., et al, *Tetrahedron Lett.* 27: 2335, 1986

Pauly, H., *Ann. Chem.* 322: 113, 1902

Rauckman, E. J., et al, *Synthetic Communications* 5(6): 409, 1975

Rozantsev, E. G., et al, *Izv. Akad. Nauk., SSSR. Ser. Khim.* 1964: 1123, 1964

Rozantsev, E. G., et al, *Tetrahedron Lett.* 21: 491, 1965a

Rozantsev, E. G., et al, *Izv. Akad. Nauk., SSSR. Ser. Khim.* 1965: 572, 1965b

Rozantsev, E. G., et al, *Izv. Akad. Nauk. SSSR. Ser. Khim.* 1966: 891, 1966

Rozantsev, E. G., p. 204 in *Free Nitroxvl Radicals*, Ulrich, H., Ed., Plenum Press, New York, 1970

Rozantsev, E. G. et al, *Izv. Akad. Nauk. SSSR. Ser. Khim.* 1968: 2364 (*Chem. Abstr.* 70:28324C)

Zabrowski, D. L., et al, *Tetrahedron Lett.* 29: 4501, 1988

We claim:

1. A method of synthesizing a nitroxide of a secondary amine, comprising the step of reacting a secondary amine with a dioxirane compound, wherein the secondary amine comprises two alpha carbon atoms attached directly to a nitrogen atom, and wherein none of the atoms attached directly to either of the two alpha carbon atoms comprises hydrogen, and wherein two molecules of the dioxirane compound are provided for each molecule of the secondary amine which is converted into a nitroxide.

2. The method of claim 1, wherein the dioxirane compound comprises dimethyldioxirane.

3. The method of claim 1, wherein the reaction is carried out in a mixture comprising a ketone solvent.

4. The method of claim 3, wherein the secondary amine is soluble in the ketone solvent.

5. The method of claim 3, wherein the secondary amine is present in particulate form in the mixture comprising the ketone solvent.

6. The method of claim 3 wherein the mixture comprises (a) a ketone solvent, and (b) a second selected solvent which increases the solubility of the secondary amine in the mixture, relative to the solubility of the secondary amine in the ketone solvent alone.

7. A method of synthesizing a nitroxide of a secondary amine, comprising the step of reacting an amine molecule with a dioxirane compound wherein the amine molecule has more than one secondary amine group, each secondary amine group comprising two alpha carbon atoms attached directly to a nitrogen atom, wherein none of the atoms attached directly to any of the alpha carbon atoms in the secondary amine groups comprises hydrogen, and wherein two molecules of the dioxirane compound are provided for each secondary amine group which is converted into a nitroxide group.

8. The method of claim 7 wherein more than one of the secondary amine groups are converted into nitroxide groups by the dioxirane compound.

9. The method of claim 7, wherein the dioxirane compound comprises dimethyldioxirane.

10. The method of claim 7, wherein the reaction is carried out in a mixture comprising a ketone solvent.

11. The method of claim 10, wherein the amine molecule is soluble in the ketone solvent.

12. The method of claim 10, wherein the amine molecule is present in particulate form in the mixture comprising the ketone solvent.

13. The method of claim 10, wherein the mixture comprises (a) a ketone solvent, and (b) a second selected solvent which increases the solubility of the secondary amine in the mixture, relative to the solubility of the secondary amine in the ketone solvent alone.

14. A mixture containing ketone molecules and a nitroxide of a secondary amine, wherein the nitroxide is created by a process comprising the step of reacting a dioxirane compound with a secondary amine having no hydrogen atoms attached directly to an alpha carbon atom, wherein at least some of the ketone molecules are created when the dioxirane compound donates an oxygen atom to the secondary amine.

15. The mixture of claim 14, wherein the dioxirane compound comprises dimethyldioxirane and the ketone comprises acetone.

16. The mixture of claim 14, wherein the dioxirane compound comprises methylethyldioxirane and the ketone comprises methylethylketone 17. The mixture of claim 14, wherein the nitroxide comprises a molecule having more than one nitroxide group.

* * * * *

UNITED STATES PATENT AND TRADEMARK OFFICE
CERTIFICATE OF CORRECTION

PATENT NO. : 5,087,752

DATED : February 11, 1992

INVENTOR(S) : Robert W. Murray and Megh Singh

It is certified that error appears in the above-identified patent and that said Letters Patent is hereby corrected as shown below:

Column 12, line 53, "I19.5" should be --119.5--

Column 13, line 11, "coldsstirred" should be --cold stirred--

Signed and Sealed this

Twentieth Day of April, 1993

Attest:

MICHAEL K. KIRK

Attesting Officer

Acting Commissioner of Patents and Trademarks